(12) United States Patent
Muroi et al.

(10) Patent No.: US 8,394,994 B2
(45) Date of Patent: Mar. 12, 2013

(54) METHOD FOR PRODUCING OF 2-ALKYL-2-CYCLOALKEN-1-ONE

(75) Inventors: Makiko Muroi, Wakayama (JP); Atsushi Nagasawa, Wakayama (JP); Kunshi Matsumoto, Wakayama (JP); Mariko Kagaya, Wakayama (JP); Hirotsugu Nishimura, Wakayama (JP); Yoshiharu Ataka, Wakayama (JP)

(73) Assignee: Kao Corporation, Tokyo (JP)

( * ) Notice: Subject to any disclaimer, the term of this patent is extended or adjusted under 35 U.S.C. 154(b) by 338 days.

(21) Appl. No.: 12/937,443

(22) PCT Filed: Apr. 2, 2009

(86) PCT No.: PCT/JP2009/056870
§ 371 (c)(1),
(2), (4) Date: Oct. 12, 2010

(87) PCT Pub. No.: WO2009/125713
PCT Pub. Date: Oct. 15, 2009

(65) Prior Publication Data
US 2011/0034722 A1 Feb. 10, 2011

(30) Foreign Application Priority Data

Apr. 11, 2008 (JP) ................................. 2008-103714
May 13, 2008 (JP) ................................. 2008-126292

(51) Int. Cl.
*C07C 45/51* (2006.01)
*C07C 69/74* (2006.01)
*C07D 305/00* (2006.01)
*C07D 309/00* (2006.01)

(52) U.S. Cl. .................. 568/341; 568/361; 560/122

(58) Field of Classification Search .................. None
See application file for complete search history.

(56) References Cited

U.S. PATENT DOCUMENTS

| 4,260,830 A | 4/1981 | Wilson et al. |
| 7,057,077 B2 * | 6/2006 | Nishimura et al. ........... 568/341 |
| 2005/0014968 A1 | 1/2005 | Mine et al. |

FOREIGN PATENT DOCUMENTS

| JP | 52-39655 | 3/1977 |
| JP | 56-147740 | 11/1981 |
| JP | 5-92934 | 4/1993 |
| JP | 2004-203844 | 7/2004 |
| JP | 2005-35939 | 2/2005 |

OTHER PUBLICATIONS

International Search Report issued Jul. 7, 2009 in International Application No. PCT/JP2009/056870.
Kenzo Takeishi, et al., "Rhodium-Catalyzed Intramolecular Hydroacylation of 5- and 6-Alkynals: Convenient Synthesis of a-Alkylidenecycloalkanones and Cycloalkenones", Chem. Eur. J., vol. 10, 2004, pp. 5681-5688.
Chin-Kang Sha, et al., "Synthesis of a Highly Hindered Hydrindanone via a-Carbonyl Radical Cyclization: Enantiospecific Formal (-)-a-Pinguisene", J. of Org. Chem., vol. 68, 2003, pp. 8704-8707.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

The present invention relates to [1] a process for producing a 2-alkyl-2-cycloalken-1-one represented by the following general formula (2), which includes the step of subjecting a 2-(1-hydroxyalkyl)cycloalkan-1-one to dehydration and isomerization in the co-existence of an acid and a platinum group metal catalyst, and [2] a process for producing an alkyl(3-oxo-alkylcycloalkyl)acetate which is useful as a perfume material, using the 2-alkyl-2-cycloalken-1-one:

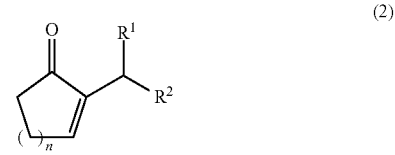

(2)

wherein n is an integer of 1 or 2; and $R^1$ and $R^2$ are each independently a hydrogen atom or an alkyl group having 1 to 8 carbon atoms with the proviso that $R^1$ and $R^2$ may form a ring through a carbon atom adjacent thereto.

9 Claims, No Drawings

METHOD FOR PRODUCING OF 2-ALKYL-2-CYCLOALKEN-1-ONE

FIELD OF THE INVENTION

The present invention relates to a process for producing 2-alkyl-2-cycloalken-1-ones, and a process for producing alkyl(3-oxo-2-alkylcycloalkyl)acetates which are useful as perfume materials, by using the 2-alkyl-2-cycloalken-1-ones.

BACKGROUND OF THE INVENTION

The 2-alkyl-2-cycloalken-1-ones are useful substances as an intermediate product for synthesis of physiologically active substances or perfume materials. Hitherto, the 2-alkyl-2-cycloalken-1-ones have been produced by first subjecting 2-(1-hydroxyalkyl)cycloalkanones to dehydration reaction to synthesize 2-(alkylidene)cycloalkanones, and then subjecting the 2-(alkylidene)cycloalkanones to isomerization reaction.

It is generally known that the above dehydration reaction is carried out in the presence of an acid. For example, Patent Documents 1 and 2 disclose the dehydration reaction using oxalic acid or phosphoric acid. Also, Patent Document 3 discloses the dehydration reaction using a solid acid.

On the other hand, there has been reported an example of the isomerization reaction using a metal catalyst. For example, Patent Document 4 discloses the isomerization reaction using a platinum group metal catalyst.

In addition, there is known the method in which the dehydration reaction and isomerization reaction are carried out only in one step. For example, Patent Document 1 discloses the method in which the dehydration reaction and isomerization reaction are carried out in one step under n-butanol reflux condition using hydrogen chloride or hydrogen bromide. Patent Document 5 discloses the method in which the reactions are carried out using hydrogen halides or sulfonic acids in the presence of an inert solvent while removing water out of the reaction system. Patent Document 6 discloses the method in which the reactions are carried out using sulfonic acids in the presence of a high-boiling solvent while removing water and 2-alkyl-2-cyclopentenone out of the reaction system.

The dehydration reaction and the isomerization reaction may be carried out separately from each other. In this case, the dehydration reaction may proceed in the presence of an acid as described in Patent Documents 1 to 3, whereas the isomerization reaction may proceed in the presence of a metal catalyst as described in Patent Document 4. However, when conducting these reactions separately, such a process tends to not only need an increased number of steps, but also become unsatisfactory in yield of the aimed product.

In the methods as described in Patent Documents 1, 5 and 6 in which the dehydration reaction and isomerization reaction are carried out in one step using an acid, the acid usable in these reactions is limited to a strong acid having a high corrosiveness against a reaction vessel used therein. As a result, in these methods, production facilities used therein are required to have a corrosion resistance. Further, 2-(alkylidene)cycloalkanones as the reaction intermediate product or 2-alkyl-2-cycloalken-1-ones as the reaction product tend to be susceptible to polymerization or decomposition, which will inevitably result in poor yield of the aimed reaction product. In addition, there tends to occur such a problem that a large amount of waste water is by-produced owing to neutralization, water-washing treatment, etc., after completion of the reactions.

Patent Document 1: JP-A 56-147740
Patent Document 2: JP-A 2004-217620
Patent Document 3: JP-A 2004-203844
Patent Document 4: JP-B 58-42175
Patent Document 5; JP-A 5-92934
Patent Document 6: JP-A 2001-261608

SUMMARY OF THE INVENTION

The present invention relates to a process for producing a 2-alkyl-2-cycloalken-1-one represented by the following general formula (2) by subjecting a 2-(1-hydroxyalkyl)cycloalkan-1-one represented by the following general formula (1) to dehydration and isomerization in the co-existence of an acid and a platinum group metal catalyst.

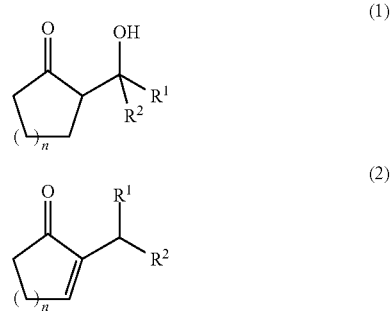

wherein n is an integer of 1 or 2; and $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto.

DETAILED DESCRIPTION OF THE INVENTION

The present invention relates to a process for producing a 2-alkyl-2-cycloalken-1-one with a high yield and a high purity, and a process for producing an alkyl(3-oxo-2-alkylcycloalkyl)acetate which is useful as a perfume material, using the 2-alkyl-2-cycloalken-1-one.

The present inventors have found that when subjecting a 2-(1-hydroxyalkyl)-cycloalkan-1-one to dehydration and isomerization in the co-existence of an acid and a platinum group metal catalyst, it is possible to synthesize the aimed compound with a high yield and a high purity.

Also, the present inventors have found that when the 2-(1-hydroxyalkyl)-cycloalkan-1-one is subjected to dehydration and isomerization in the co-existence of an acid and a platinum group metal catalyst as well as in a hydrogen gas atmosphere in which a concentration of a hydrogen gas varies with time, it is possible to synthesize the aimed compound with a high yield and a high purity.

Thus, the present invention relates to the following aspects [1] to [3].

[1] A process for producing a 2-alkyl-2-cycloalken-1-one represented by the following general formula (2) (hereinafter occasionally referred to merely as a "compound (2)"), including the step of subjecting a 2-(1-hydroxyalkyl)cycloalkan-1-one represented by the following general formula (1) (hereinafter occasionally referred to merely as a "compound (1)") to dehydration and isomerization in the co-existence of an acid and a platinum group metal catalyst:

$$\text{(1)}$$

wherein n is an integer of 1 or 2; and $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto.

[2] The process for producing the compound (2), wherein the dehydration and isomerization step includes a step (A) and a step (B) to be conducted subsequent to the step (A), Step (A): subjecting the compound (1) to dehydration and isomerization in an atmosphere in which a concentration of a hydrogen gas is from 5 to 45% by volume; and Step (B): subjecting the compound (1) to dehydration and isomerization in an atmosphere in which a concentration of a hydrogen gas is 1% by volume or higher, and is lower, by 2% by volume or more, than the concentration of the hydrogen gas in the atmosphere used in the step (A).

[3] A process for producing an alkyl(3-oxo-alkylcycloalkyl) acetate represented by the following general formula (4), including the steps of:

reacting the compound (2) with a malonic acid diester represented by the following general formula (3); and reacting the resulting reaction product with water:

$$\begin{array}{c} COOR^3 \\ | \\ CH_2 \\ | \\ COOR^3 \end{array} \quad (3)$$

wherein $R^3$ is an alkyl group having 1 to 3 carbon atoms with the proviso that the two $R^3$ groups may be the same or different from each other; and $$\text{(4)}$$

wherein n, $R^1$, $R^2$ and $R^3$ are the same as defined above.

[Compounds (1) and (2)]

In the process for producing the compound (2) according to the present invention, the compound (1) is used as a raw material thereof.

In the above general formulae (1) and (2), $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto. $R^1$ and $R^2$ are each preferably a hydrogen atom or a straight-chain or branched alkyl group, and more preferably a hydrogen atom or a straight-chain alkyl group.

Examples of the alkyl group as $R^1$ and $R^2$ include a methyl group, an ethyl group, a propyl group, an isopropyl group, various butyl groups, various pentyl groups, various hexyl groups, various heptyl groups and various octyl groups.

The clause "$R^1$ and $R^2$ may form a cyclopentane ring or a cyclohexane ring through a carbon atom adjacent thereto" as used herein means that "$R^1$ may be bonded to $R^2$ through the carbon atom, or $R^2$ may be bonded to $R^1$ through the carbon atom, to form a 5-membered ring or a 6-membered ring". Meanwhile, hydrogen atoms bonded to the carbon atom may be substituted, for example, with a hydrocarbon group such as an alkyl or alkenyl group having 1 to 5 carbon atoms.

Specific examples of the compound (1) include 2-(1-hydroxypropyl)-cyclopentanone, 2-(1-hydroxybutyl)-cyclopentanone, 2-(1-hydroxypentyl)-cyclopentanone, 2-(1-hydroxyhexyl)-cyclopentanone, 2-(1-hydroxy-1-methylbutyl)-cyclopentanone, 2-(1-hydroxy-2-methylbutyl)-cyclopentanone, 2-(1-hydroxycyclopentyl)-cyclopentanone, 2-(1-hydroxycyclohexyl)-cyclopentanone, 2-(1-hydroxypropyl)-cyclohexanone, 2-(1-hydroxybutyl)-cyclohexanone, 2-(1-hydroxypentyl)-cyclohexanone, 2-(1-hydroxyhexyl)-cyclohexanone, 2-(1-hydroxy-1-methylbutyl)-cyclohexanone, 2-(1-hydroxy-2-methylbutyl)-cyclohexanone, 2-(1-hydroxycyclopentyl)-cyclohexanone and 2-(1-hydroxycyclohexyl)-cyclohexanone. Among these compounds (1), preferred are 2-(1-hydroxypropyl)-cyclopentanone, 2-(1-hydroxybutyl)-cyclopentanone, 2-(1-hydroxypentyl)-cyclopentanone and 2-(1-hydroxyhexyl)-cyclopentanone, and especially preferred is 2-(1-hydroxypentyl)-cyclopentanone.

Specific examples of the compound (2) include 2-propyl-2-cyclopenten-1-one, 2-butyl-2-cyclopenten-1-one, 2-pentyl-2-cyclopenten-1-one, 2-hexyl-2-cyclopenten-1-one, 2-(1-methylbutyl)-2-cyclopenten-1-one, 2-(2-methylbutyl)-2-cyclopenten-1-one, 2-cyclopentyl-2-cyclopenten-1-one, 2-cyclohexyl-2-cyclopenten-1-one, 2-propyl-2-cyclohexen-1-one, 2-butyl-2-cyclohexen-1-one, 2-pentyl-2-cyclohexen-1-one, 2-hexyl-2-cyclohexen-1-one, 2-(1-methylbutyl)-2-cyclohexen-1-one, 2-(2-methylbutyl)-2-cyclohexen-1-one, 2-cyclopentyl-2-cyclohexen-1-one and 2-cyclohexyl-2-cyclohexen-1-one. Among these compounds (2), preferred are 2-propyl-2-cyclopenten-1-one, 2-butyl-2-cyclopenten-1-one, 2-pentyl-2-cyclopenten-1-one and 2-hexyl-2-cyclopenten-1-one, and especially preferred is 2-pentyl-2-cyclopenten-1-one.

[Method for Producing Compound (1)]

The compound (1) may be produced by known methods. For example, the compound (1) may be produced by reacting a cycloalkanone having 5 or 6 carbon atoms with an aldehyde or a ketone represented by the following formula (6).

In the present invention, the compound (1) produced by the above method may be used as such without being purified, but may also be purified before use by distillation, etc., when the catalyst used in the method is deteriorated in catalytic activity.

$$\text{(6)}$$

wherein R¹ and R² are the same as defined above.
[Process for Producing Compound (2)]

In the present invention, the compound (2) is produced by subjecting the compound (1) to dehydration and isomerization reaction in the co-existence of an acid and a platinum group metal catalyst.

<Acid>

In the present invention, as the acid, there may be used an inorganic acid, an organic acid and a solid acid, etc.

(Inorganic Acid and Organic Acid)

The inorganic acid and the organic acid used in the present invention may be ordinary inorganic and organic acids. Specific examples of the acid include inorganic acids such as hydrochloric acid, sulfuric acid, phosphoric acid, orthophosphoric acid, and condensed phosphoric acids such as metaphosphoric acid, pyrophosphoric acid and tripolyphosphoric acid; and organic acids such as acetic acid, oxalic acid, citric acid, maleic acid, fumaric acid and malic acid.

Among these acids, from the viewpoint of suppressing corrosion of metals, preferred are those acids having a first acid dissociation constant (pKa) of 0 or more and preferably 0.5 or more as measured at 25° C. More specifically, as the preferred acids, there may be mentioned phosphoric acid (first pKa: 2.15), condensed phosphoric acids such as pyrophosphoric acid (first pKa: 0.8) and tripolyphosphoric acid, and organic acids such as acetic acid (first pKa: 4.56), oxalic acid (first 1.04), citric acid (first pKa: 2.87), maleic acid (first pKa: 1.75), fumaric acid (first pKa: 2.85) and malic acid (first pKa: 3.24).

In addition, from the viewpoint of boiling point, more preferred are phosphoric acid, condensed phosphoric acids such as pyrophosphoric acid and tripolyphosphoric acid, and organic acids such as oxalic acid, citric acid, maleic acid, fumaric acid and malic acid, and especially preferred are phosphoric acid and oxalic acid.

The acid dissociation constant (pKa) as used in the present invention is described, for example, in "Chemical Handbook", The Chemical Society of Japan (revised 3rd edition, published by Maruzen K. K. on Jun. 25, 1984).

These acids may be supported on a carrier. Examples of the carrier include silica and activated carbon. Among these carriers, preferred is activated carbon. The acid may be supported on the carrier by the method in which the carrier is impregnated with the acid, and the method in which phosphoric acid is added and penetrated into a wood material (such as sawdust and wood chips) at a high temperature while suppressing generation of tar to erode fibers of the wood material, and then the thus treated wood material is subjected to carbonization reaction at a temperature of from 500 to 700° C. under air-free conditions to obtain a phosphoric acid-supporting activated carbon (also referred to as a "phosphoric acid-activated carbon"). Among these acid-supporting carriers, the phosphoric acid-supporting activated carbon is especially preferred.

Such an acid supported on the carrier can be handled in the same manner as the below-mentioned solid acid, and is readily separated and removed from the reaction mixture.

These acids may be used alone or in combination of any two or more thereof.

(Solid Acid)

As the solid acid, there may be used conventionally known solid acids. Specific examples of the solid acid include inorganic metal solids such as activated alumina, zirconia sulfate, metal phosphates, aluminum dihydrogen tripolyphosphate and titanium oxide; cation exchange resins; silica-titania composite oxide, silica-calcium oxide composite oxide, silica-magnesia composite oxide and zeolite.

The solid acid used in the present invention preferably satisfies such a condition in which an amount (mmol/g) of acid sites of the solid acid from which $NH_3$ is desorbed at a temperature of from 100 to 250° C. is larger than an amount (mmol/g) of acid sites of the solid acid from which $NH_3$ is desorbed at a temperature higher than 250° C., as measured by an ammonia temperature-programmed desorption (TPD) method. The amount of acid sites of the solid acid from which $NH_3$ is desorbed at a temperature of from 100 to 250° C. is preferably 0.3 mmol/g or more, whereas the amount of acid sites of the solid acid from which $NH_3$ is desorbed at a temperature higher than 250° C. is preferably less than 0.3 mmol/g.

The amount of acid sites of the solid acid by ammonia TPD is determined as a relative amount based on an amount (0.99 mmol/g) of acid sites of zeolite; JRC-Z5-25H as a reference catalyst prescribed by The Catalysis Society of Japan, which is measured at a high peak (peak on a high-temperature side among two kinds of peaks observed). The peak is detected by quantitative determination of ammonia using a fragment m/e=16 of the ammonia in a mass spectrum.

The TPD (temperature-programmed desorption) may be measured by an ordinary method generally used therefor. For example, the TPD measurement may be carried out after sequentially conducting a pretreatment, an $NH_3$ absorption treatment and a vacuum treatment under the following conditions.

Pretreatment: Temperature is raised up to 200° C. in helium atmosphere over 20 min, and maintained at the same temperature for 1 h;

$NH_3$ absorption treatment: $NH_3$ is absorbed at 50° C. under 2.7 kPa for 10 min;

Vacuum treatment: Treated at 50° C. for 4 h; and

TPD measurement: While flowing a helium gas at a rate of 50 mL/min, temperature is raised up to 600° C. at a rate of 5° C./min.

As the solid acid having such an acid site distribution, there are preferably used, for example, those solid acids having at least one of the following structure (A), the following structure (B) and the following metal atom (C). Among these solid acids, preferred are the solid acids having the structure (A) and the metal atom (C), the solid acids having the structure (B) and the metal atom (C), and the solid acids having the structure (A), the structure (B) and the metal atom (C).

Structure (A): Structure in which a hydrogen is removed from at least one OH group contained in an inorganic phosphoric acid.

Structure (B): Structure in which a hydrogen is removed from at least one OH group contained in an organic phosphoric acid represented by the following general formula (7) or (8).

Metal atom (C): One or more metal atoms selected from the group consisting of aluminum, gallium and iron.

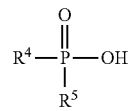

(7)

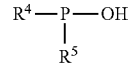

(8)

wherein $R^4$ and W are each selected from $R^{10}$, $OR^{10}$, OH and H with the proviso that at least one of $R^4$ and $R^5$ is $R^{10}$ or $OR^{10}$ wherein $R^{10}$ is an organic group having 1 to 22 carbon atoms, preferably an organic group having 1 to 15 carbon atoms, and more preferably an organic group having 1 to 6 carbon atoms.

As the structure (A), there may be mentioned the structures derived from orthophosphoric acid, condensed phosphoric acids such as metaphosphoric acid and pyrophosphoric acid, etc. Among these structures, from the viewpoint of good performance, preferred is the structure (A) derived from orthophosphoric acid.

Examples of the organic phosphoric acid represented by the general formula (7) or (8) in the structure (B) include phosphonic acid, phosphonic acid monoesters, phosphinic acid, phosphoric acid monoesters, phosphoric acid diesters, phosphorous acid monoesters and phosphorous acid diesters. Among these structures, preferred is the structure (B) derived from phosphonic acid.

$R^{10}$ is preferably an organic group preferably having 1 to 15 carbon atoms and more preferably 1 to 8 carbon atoms. Examples of the organic group as $R^{10}$ include an alkyl group such as a methyl group, an ethyl group, a propyl group, an isopropyl group, various butyl groups, various pentyl groups, various hexyl groups and various octyl groups; and an aryl group such as a phenyl group and a 3-methyl phenyl group.

As the metal atom (C), aluminum is preferred from the viewpoint of good performance and/or low costs. Meanwhile, for the purpose of improving a selectivity and other performances, the metal atom (C) may contain a small amount of a metal atom other than aluminum, gallium and iron. Also, it is not particularly required that a whole of the metal atom (C) contained in the catalyst is bonded to the structure (A) or (B), and only a part of the metal atom (C) may be present in the form of a metal oxide or a metal hydroxide.

The solid acid may be produced by a precipitation method, a method of impregnating a metal oxide or a metal hydroxide with an inorganic phosphoric acid and an organic phosphoric acid, a method of substituting an inorganic phosphoric acid group contained in an inorganic aluminum phosphate gel with an organic phosphoric acid group, etc. Among these methods, preferred is the precipitation method.

Upon production of the solid acid, a carrier having a large surface area may be allowed to coexist therewith to obtain a supported catalyst. Examples of the carrier include silica, alumina, silica/alumina, titania, zirconia, diatomaceous earth and activated carbon. When the carrier is used in an excessive amount, the resulting supported catalyst tends to be deteriorated in catalytic activity owing to a low content of the active component. Therefore, the content of the carrier in the catalyst is preferably 90% by weight or less.

The solid acid may be in the form of either a powder or a molded product. In addition, the solid acids may have the same composition or may be used in combination of two or more kinds thereof which are different in composition from each other.

The above inorganic acids, organic acid and solid acids may be respectively used alone or in combination of any two or more thereof. When using the solid acid solely, the neutralization step may be omitted.

The amount of the acid used is preferably 0.0001% by mass or more on the basis of the raw material from the viewpoint of good reactivity. On the other hand, from the viewpoint of suppressing occurrence of polymerization between double bond-containing compounds produced and thereby enhancing a yield of the aimed product, the amount of the acid used is preferably 25% by mass or more. From the above viewpoints, the amount of the acid used is more preferably from 0.001 to 12% by mass and still more preferably from 0.01 to 6% by mass.

<Platinum Group Metal Catalyst>

The platinum group metal catalyst used in the present invention contains one or more metal components selected from the group consisting of osmium (Os), ruthenium (Ru), iridium (Ir), rhodium (Rh), platinum (Pt) and palladium (Pd) belonging to elements of Groups 8 to 10 in the 5th and 6th periods of the Periodic Table as main components. Among these metal components, from the viewpoint of catalytic activity, etc., Pt and Pd are preferred, and Pd is more preferred. These metal components may be used alone or in combination of any two or more thereof. The term "containing the metal components as main components" as used herein means the metal components are preferably contained in an amount of 50 mol % or more, more preferably 70 mol % or more, still more preferably 90 mol % or more, and further still more preferably 95 mol % or more in the catalyst metal components.

The platinum group metal catalyst may also contain other metal components or may contain a co-catalyst only in an auxiliary amount. Examples of the other metal components include elements of Groups 4 to 11 in the 4th period of the Periodic Table such as Ti, V, Cr, Mn, Fe, Co, Ni and Cu, as well as W, Ag and Au.

The catalyst may be formed into an appropriate configuration such as a supporting type, a Raney type, a homogeneous type, a powder type and a granule type when used in the process.

The supporting type catalyst is a catalyst of such a type in which the metal components are supported on a carrier in order to improve physical properties thereof such as durability. The supporting type catalyst may be prepared by known methods such as a precipitation method, an ion exchange method, an evaporation-to-dryness method, a spray-drying method and a kneading method. Examples of the carrier include carbon (activated carbon), alumina, silica, silica-alumina, barium sulfate and calcium carbonate. Among these carriers, preferred are carbon (activated carbon), silica, alumina and silica-alumina.

Specific examples of the palladium catalyst used as the catalyst include palladium on carbon, palladium on alumina, palladium on barium sulfate and palladium on calcium carbonate. Among these palladium-supporting catalysts, palladium on carbon and palladium on alumina are preferred because they have a high activity to the reaction and can be readily recovered from the reaction mixture after completion of the reaction, and palladium on carbon is especially preferred from the viewpoints of a good availability, easiness of handing and a high activity to the reaction.

The amount of the metal components supported on the carrier in the supporting type catalyst is usually from 0.1 to 70% by mass on the basis of a total amount of the carrier and the metal components supported thereon from the viewpoint of good catalytic activity.

The Raney type catalyst is a porous spongy metal catalyst, and may be prepared by the method described, for example, in Teruo KUBOMATSU and Shinichiro KOMATSU "Raney Catalysts", Kyoritsu-Shuppan (1971), etc.

When using the homogeneous type catalyst, for example, an aqueous solution containing a metal salt of an acid such as nitric acid and hydrochloric acid, or a mixed aqueous solution of various metal salts, may be added dropwise to the reaction system.

Meanwhile, as the above catalyst, there may also be used commercially available products.

The amount of the platinum group metal catalyst used in the above process may be optimized according to the type of the reaction.

In the case of the batch type reaction, from the viewpoints of a good reactivity and economy, the platinum group metal catalyst is preferably used in an amount of from 0.0002 to 3% by mass, more preferably from 0.002 to 2% by mass and still more preferably from 0.005 to 1% by mass in terms of an amount of the metal on the basis of the compound (1) as the raw material.

The acid and the platinum group metal catalyst may be used in respective separate forms or may be used as an integrated catalyst having one configuration. For example, if the platinum group metal catalyst is supported on an acid carrier, it is not required to separately add an additional acid thereto.

The acid and the platinum group metal catalyst may also be used either in a suspended bed or a fixed bed.

The fixed bed reaction using the carrier-supported acid or the solid acid is effective for mass-production of the aimed compound because no step of separating the catalyst, etc., from the final reaction product is required.

Even in the suspended bed reaction, as far as the solid acid is used therein, the catalyst, etc., may be readily separated by filtration, etc., from the reaction solution, so that the thus separated catalyst can be suitably recycled. The reaction may be carried out in either a liquid phase or a vapor phase, and by either a batch method or a continuous method.

<Dehydration and Isomerization Reaction>

The platinum group metal catalyst may be activated by a reducing gas such as a hydrogen gas. Therefore, the dehydration and isomerization reaction may be carried out in the presence of the reducing gas or under a flow of the reducing gas.

The dehydration and isomerization reaction preferably includes the following step (A) and the following step (B) to be conducted subsequent to the step (A).

Step (A): subjecting the compound (1) to dehydration and isomerization in an atmosphere in which a concentration of a hydrogen gas is from 5 to 45% by volume; and Step (B): subjecting the compound (1) to dehydration and isomerization in an atmosphere in which a concentration of a hydrogen gas is 1% by volume or higher, and is lower, by 2% by volume or more, than the concentration of the hydrogen gas in the atmosphere used in the step (A).

(Concentration of Hydrogen Gas)

The concentration of the hydrogen gas used in the former step (A) is from 5 to 45% by volume and preferably from 5 to 40% by volume from the viewpoint of well activating the platinum group metal catalyst. In some cases, the concentration of the hydrogen gas used in the former step (A) is preferably from 15 to 45% by volume and more preferably from 15 to 40% by volume.

On the other hand, the concentration of the hydrogen gas used in the latter step (B) is 1% by volume or higher and is lower, by 2% by volume or more, than the concentration of the hydrogen gas used in the step (A), preferably 1.5% by volume or higher and is lower, by 2% by volume or more, than the concentration of the hydrogen gas used in the step (A), and more preferably 2% by volume or higher and is lower, by 3% by volume or more, than the concentration of the hydrogen gas used in the step (A), from the viewpoint of suppressing by-production of the below-mentioned compound (9).

Also, in some cases, the concentration of the hydrogen gas used in the latter step (B) is preferably 5% by volume or higher and is lower, by 2% by volume or more, than the concentration of the hydrogen gas used in the step (A), more preferably 5% by volume or higher and is lower, by 5% by volume or more, than the concentration of the hydrogen gas used in the step (A), and still more preferably 5% by volume or higher and is lower, by 8% by volume or more, than the concentration of the hydrogen gas used in the step (A).

The concentration of the hydrogen gas used in the step (A) or (B) may be kept constant or may vary as long as the hydrogen gas concentration lies within the above-specified range.

The hydrogen gas is preferably used in the form of a mixed gas with an inert gas.

The dehydration and isomerization reaction is more preferably carried out in an atmosphere of a mixed gas composed of a reducing gas such as a hydrogen gas and an inert gas or under a flow of the mixed gas. Examples of the preferred inert gas include a nitrogen gas, an argon gas and a helium gas. Among these inert gases, more preferred is a nitrogen gas.

From the viewpoint of suppressing by-production of the below-mentioned compound (9), the concentration of the reducing gas used in the above atmosphere is preferably 80% or less, more preferably 50% or less and still more preferably 30% or less, whereas the concentration of the reducing gas used under the above gas flow may be adequately optimized depending upon a flowing amount of the gas.

In the dehydration and isomerization reaction using the reducing gas, a double bond of a part of the intermediate product and/or the reaction product is reduced to produce a 2-alkylcycloalkan-1-one represented by the following general formula (9) (hereinafter occasionally referred to merely as a "compound (9)").

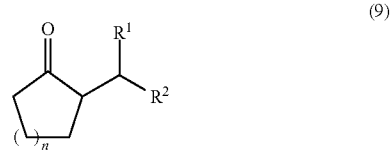

(9)

wherein n, $R^1$ and $R^2$ are the same as defined above.

(Reaction Conditions of Dehydration and Isomerization)

The reaction temperature used in the dehydration and isomerization reaction of the present invention is preferably from 70 to 300° C. The reaction temperature is more preferably from 90 to 200° C., still more preferably from 100 to 170° C., and especially preferably from 130 to 160° C., from the viewpoints of completing the reaction for a short period of time and preventing polymerization and decomposition of the compound (2) to enhance a yield thereof.

The dehydration and isomerization reaction is allowed to proceed under normal pressures. However, when the dehydration and isomerization reaction is carried out under reduced pressure, it is possible to efficiently distill off water produced out of the reaction system without distilling off the raw material and the reaction product, thereby enabling the reaction to proceed in a more efficient manner. The reaction pressure is preferably adjusted to the range of from 20 to 200 kPa and more preferably from 50 to 150 kPa depending upon the reaction temperature used. In the process of the present invention, the dehydration and isomerization reaction is preferably carried out while distilling off water produced out of the reaction system.

From the viewpoint of producing the compound (2) with a high yield and a high purity, the reaction time used in the dehydration and isomerization reaction is controlled such that the reaction time of the step (A) is preferably from 5 to 50%, more preferably from 10 to 40% and still more preferably from 10 to 35% of a total reaction time of the steps (A) and (B).

<Solvent>

The process of the present invention may be carried out either in the presence of a solvent or under a solvent-free condition. The process of the present invention is advantageously carried out under a solvent-free condition from the viewpoints of a good productivity and economy. The solvent used in the process of the present invention is not particularly limited, and may be an inert organic solvent. Examples of the inert organic solvent include alcohols such as methanol, ethanol, propanol, isopropanol, isobutanol, tert-butanol, n-butanol, 2-butanol, isopentanol, pentanol, hexanol, 2-ethyl butanol, heptanol, 2-heptanol, octanol, 2-octanol, cyclopentanol, cyclohexanol, ethylene glycol, propylene glycol, ethylene glycol monoethyl ether, ethylene glycol monopropyl ether, propylene glycol monoethyl ether, diethylene glycol, diethylene glycol monomethyl ether, benzyl alcohol and phenyl ethanol; ketones such as methyl ethyl ketone, methyl isopropyl ketone, methyl propyl ketone, methyl isobutyl ketone, methyl n-butyl ketone, methyl n-amyl ketone, methyl isoamyl ketone, ethyl butyl ketone, methyl n-hexyl ketone, dipropyl ketone, diisobutyl ketone, cyclopentanone and cyclohexanone; ethers such as isopropyl ether, n-butyl ether, 1,4-dioxane, isoamyl ether, n-hexyl ether, tetrahydropyran 2-methyl furan, diethylene glycol diethyl ether, methyl phenyl ether and ethyl phenyl ether; esters such as n-methyl formate, n-propyl formate, n-butyl formate, methyl acetate, isopropyl acetate, n-butyl acetate, n-amyl acetate, n-hexyl acetate, cyclohexyl acetate, ethyl propionate, n-butyl propionate, methyl butyrate, n-butyl butyrate, methyl isovalerate, ethyl lactate, methyl benzoate, propyl benzoate, dimethyl phthalate, diethyl oxalate, dimethyl succinate, dimethyl glutarate and dimethyl adipate; and hydrocarbons such as n-hexane, n-octane, n-decane, ligroin, cyclohexane, benzene, toluene, xylene, ethyl benzene, isopropyl benzene, amyl benzene, t-butyl benzene, p-cymene, tetralin and decalin. These solvents may be used alone or in combination of any two or more thereof.

The amount of the solvent used in the process of the present invention is preferably from 0.1 to 5 times and more preferably from 0.3 to 2 times by mass on the basis of the compound (1) as the raw material.

In the process for producing the compound (2), it is possible to prevent polymerization of the 2-(alkylidene)cycloalkanone as the intermediate reaction product and the 2-alkyl-2-cycloalken-1-one as the final reaction product, so that the compound (2) can be produced with a high yield and a high purity. In addition, it is possible to produce the aimed compound by using the acid and the platinum group metal catalyst which have a low corrosiveness and a low toxicity, reuse the acid and the platinum group metal catalyst, and obtain the aimed compound under a solvent-free condition.

[Process for Producing Compound (4)]

When using the compound (2) obtained by the above production process as a raw material, it is possible to produce an alkyl(3-oxo-alkylcycloalkyl)acetate represented by the following general formula (4) which is useful as a perfume material or a physiologically active substance (hereinafter occasionally referred to merely as a "compound (4)"), for example, by the method as described in JP-A 56-147740.

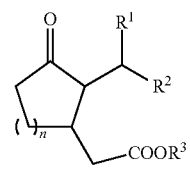

wherein n, $R^1$ and $R^2$ are the same as defined above; and $R^3$ is an alkyl group having 1 to 3 carbon atoms, preferably a straight-chain or branched alkyl group having 1 to 3 carbon atoms.

More specifically, the compound (2) is first reacted with a malonic acid diester represented by the following general formula (3) in the presence of a base to obtain a compound represented by the following general formula (11) (hereinafter occasionally referred to merely as a "compound (11)").

The amount of the compound (3) to be reacted with the compound (2) as the raw material is preferably from 1 to 5 times and preferably from 1.2 to 2 times moles of the compound (2) used.

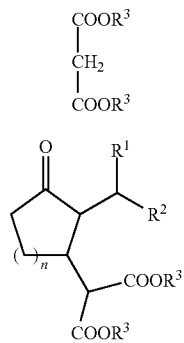

wherein n, $R^1$, $R^2$ and $R^3$ are the same as defined above, and the two $R^2$ groups may be the same or different from each other.

Examples of the base usable in the above process include alkali metals such as sodium and potassium; and alkali metal alkoxides such as sodium alkoxides and potassium alkoxides.

The amount of the base used is preferably from 0.005 to 0.2 time and more preferably from 0.01 to 0.1 time moles of the compound (2) used. Examples of the preferred solvent include polar solvents such as alcohols.

The reaction temperature used in the above process is preferably from −10 to 30° C. and more preferably from −2 to 20° C.

Next, the thus obtained compound (11) is reacted with water to produce the compound (4). The amount of water to be reacted is preferably from 1 to 3 times moles of the compound (11) used. The reaction is preferably carried out while adding water dropwise into the reaction system. In this case, the reaction temperature is preferably from 150 to 230° C. and more preferably from 180 to 220° C.

The thus obtained compound (4) has a higher yield and a less content of impurities as compared to those obtained by the conventional processes. Therefore, it is possible to reduce a load for purification of the compound (4) in order to produce the compound (4) having a high purity. Thus, the compound (4) can provide an excellent perfume material.

EXAMPLES

In the following Examples and Comparative Examples, the term "%" represents "% by mass" unless otherwise specified. In addition, all of the reaction pressures used hereinafter represent 101 kPa (atmospheric pressure).

The quantitative determination of respective reaction products was carried out by gas chromatography (GC) ("6890N" with a column "DB-1" (30 m×0.25 mm×0.25 μm) available from Agilent Technology Corp.; oven: 100° C.→5° C./min→210° C.→20° C./min→280° C. (held for 4.5 min) (total 30 min); carrier: He; flow rate: 1.6 mL/min; inlet temperature: 200° C.; detector (FID) temperature: 280° C.; amount charged: 1 μL; split: 100:1) according to an internal standard method (internal standard: undecane (purity: 99%; available from Nacalai Tesque, Inc.)).

Synthesis Example 1

Synthesis of 2-(1-hydroxypentyl)-cyclopentan-1-one

A 6 m³ reaction vessel equipped with a dropping tank was charged with 2241 kg (26.6 kmol) of cyclopentanone, 1007 kg of water and 11 kg of 48% NaOH. The contents of the reaction vessel were cooled to 15° C. while stirring, and then 985 kg (11.4 kmol) of valeraldehyde were added dropwise thereto at the same temperature over 5 h, followed by stirring the resulting mixture for 1 h. After completion of the reaction, an excess amount of cyclopentanone was recovered by distillation. As a result, it was confirmed that 1868 kg of the final reaction product obtained from an organic layer of the reaction mixture contained 1706 kg of 2-(1-hydroxypentyl)-cyclopentan-1-one.

Production Example 1

Production of Solid Acid: EtP-AlPO4

Ethylphosphonic acid (available from Aldrich Corp.; purity: 98%), 85% orthophosphoric acid (available from Kishida Chemical Co., Ltd.) and aluminum nitrate (nonahydrate) (available from Aldrich Corp.; purity: 98%) were weighed in amounts of 9.9 g, 27.7 g and 112.5 g, respectively, and dissolved in 1000 g of water. Then, an ammonia aqueous solution (available from Kishida Chemical Co., Ltd.) was added dropwise to the resulting mixed solution at room temperature to increase a pH of the mixed solution up to 5. In the course of the dropping, a gel-like white precipitate was produced. The thus obtained precipitate was separated from the reaction solution by filtration, washed with water, and then dried at 110° C. for 15 h. The resulting dried solid was pulverized into particles having a size of 60 mesh or less and then calcined at 250° C. for 3 h to obtain a solid acid: EtP-AlPO$_4$.

The thus obtained solid acid was measured for contents of metal, phosphorus and carbon therein using an ICP emission spectrophotometer ("ICPS1000III" available from Shimadzu Corp.) and a CHN element analyzer ("2400-2" available from Perkin Elmer Co., Ltd.). As a result, it was confirmed that the solid acid had a metal content of 16%, a phosphorus content of 19% and a carbon content of 2.5%, and an molar ratio (x) of an organic phosphoric acid therein was 0.17.

In addition, the amount of acid sites of the resulting solid acid was measured by ammonia temperature-programmed desorption (TPD) method under the following conditions:

[measuring apparatus: "Multi-Task TPD" available from Bel Japan, Inc.; measuring conditions: (pretreatment) the solid acid was heated to 200° C. in helium atmosphere over 20 min and held for 1 h; (NH$_3$ adsorption treatment) NH$_3$ was adsorbed on the solid acid at 50° C. under 2.7 kPa for 10 min; (vacuum treatment) the solid acid was treated in vacuo at 50° C. for 4 h; (TPD measurement) while flowing a helium gas at a rate of 50 mL/min, the solid acid was heated to 600° C. at a temperature rise rate of 5° C./min; the amount of acid sites of the solid acid was determined as a relative amount based on an amount (0.99 mmol/g) of acid sites of zeolite; JRC-Z5-25H as a reference catalyst prescribed by The Catalysis Society of Japan, which was measured at a high peak (peak on a high-temperature side among two kinds of peaks observed)]. As a result, it was confirmed that the amount of acid sites of the solid acid from which ammonia was desorbed at a temperature of from 100 to 250° C. was 0.74 mmol/g, and the amount of acid sites of the solid acid from which ammonia was desorbed at a temperature higher than 250° C. was 0.06 mmol/g.

Example I-1

A 200 mL three-necked separable flask (made of glass) equipped with a dehydration apparatus was charged with 100.0 g (0.499 mol) of 2-(1-hydroxypentyl)-cyclopentan-1-one (purity: 85%) obtained according to the method described in Synthesis Example 1, 1.93 g of a phosphoric acid-supporting activated carbon (H$_3$PO$_4$/C; available from Taihei Chemical Industrial Co., Ltd.; powder, 22.1% hydrous product; phosphorus content: 0.012 (elemental analysis)), and 7.25 g of 5% Pd/C (available from Evonik Degussa Japan Co., Ltd.; powder, 58.6% hydrous product). The contents of the flask were mixed with each other under heating in an atmosphere containing hydrogen and nitrogen at a volume ratio (hydrogen:nitrogen) of 1:4 at 140° C. under 101 kPa (ordinary pressure).

After 10 h from initiation of the reaction, 17.47 g of a fraction was obtained. As a result of subjecting the obtained final reaction product to quantitative determination by GC, it was confirmed that 67.1 g (0.441 mol) of 2-pentyl-2-cyclopenten-1-one (compound A shown in Table 1) were produced, and 5.3 g (0.035 mol) of 2-pentylcyclopentan-1-one (compound B shown in Table 1) were by-produced. Further, it was confirmed that the yield of 2-pentyl-2-cyclopenten-1-one was 89%. The results including those for the other by-products are collectively shown in Table 1.

Example I-2

A 200 mL four-necked separable flask (made of glass) equipped with a dehydration apparatus was charged with 50.0 g (0.238 mol) of 2-(1-hydroxypentyl)-cyclopentan-1-one (purity: 81%) obtained according to the method described in Synthesis Example 1, 0.77 g (0.16 mmol) of 2% phosphoric acid (prepared by diluting 85% phosphoric acid available from Kishida Chemical Co., Ltd., with ion-exchanged water), and 4.9 g of 5% Pd/C (available from N.E. ChemCat Corp.;

powder, 49% hydrous product; pH=5.8). The contents of the flask were mixed with each other under heating in an atmosphere containing hydrogen and nitrogen at a volume ratio (hydrogen:nitrogen) of 1:7 at 150° C. under 101 kPa.

After 12 h from initiation of the reaction, 8.58 g of a fraction was obtained. As a result of subjecting the obtained final reaction product to quantitative determination by GC, it was confirmed that 30.6 g (0.201 mol) of 2-pentyl-2-cyclopenten-1-one were produced, and 2.9 g (0.019 mol) of 2-pentylcyclopentan-1-one were by-produced. Further, it was confirmed that is the yield of 2-pentyl-2-cyclopenten-1-one was 84%. The results including those for the other by-products are collectively shown in Table 1.

Example I-3

A 200 mL four-necked separable flask equipped with a dehydration apparatus was charged with 50.4 g (0.240 mol) of 2-(1-hydroxypentyl)-cyclopentan-1-one (purity: 81%) obtained according to the method described in Synthesis Example 1, 0.18 g (1.56 mmol) of 85% phosphoric acid and 4.9 g of 5% Pd/C (shape: powder; 49% hydrous product; pH=5.8). The contents of the flask were mixed with each other under heating in an atmosphere containing hydrogen and nitrogen at a volume ratio (hydrogen:nitrogen) of 1:7 at 150° C. under 101 kPa.

After 11 h from initiation of the reaction, 8.32 g of a fraction was obtained. As a result of subjecting the obtained final reaction product to quantitative determination by GC, it was confirmed that 28.8 g (0.189 mol) of 2-pentyl-2-cyclopenten-1-one and 1.5 g (0.010 mol) of 2-pentylcyclopentan-1-one were produced. Further, it was confirmed that the yield of 2-pentyl-2-cyclopenten-1-one was 79%. The results including those for the other by-products are collectively shown in Table 1.

Example I-4

The final reaction product obtained in Example I-3 was filtered to separate the catalyst therefrom. The thus separated catalyst was mixed with 43.3 g (0.206 mol) of 2-(1-hydroxypentyl)-cyclopentan-1-one (purity: 81%) obtained according to the method described in Synthesis Example 1, and the resulting mixture was mixed under heating in the same conditions as in Example I-3.

After 9.5 h from initiation of the reaction, 5.35 g of a fraction was obtained. As a result of analysis of the obtained final reaction product, it was confirmed that 26.5 g (0.174 mol) of 2-pentyl-2-cyclopenten-1-one and 2.5 g (0.016 mol) of 2-pentylcyclopentan-1-one were produced. Further, it was confirmed that the yield of 2-pentyl-2-cyclopenten-1-one was 85%. The results including those for the other by-products are collectively shown in Table 1. From the results shown in Table 1, it was recognized that even when the recycled catalyst was used, 2-pentyl-2-cyclopenten-1-one was produced with the comparable yield.

Example I-5

A 200 mL four-necked separable flask equipped with a dehydration apparatus was charged with 50.8 g (0.243 mol) of 2-(1-hydroxypentyl)-cyclopentan-1-one (purity: 81%) obtained according to the method described in Synthesis Example 1, 0.13 g of the solid acid (shape: powder) obtained in Production Example 1 and 5.03 g of 5% Pd/C (powder; 49% hydrous product; pH=5.8). The contents of the flask were mixed with each other under heating in an atmosphere containing hydrogen and nitrogen at a volume ratio (hydrogen:nitrogen) of 1:7 at 150° C. under 101 kPa.

After 15.5 h from initiation of the reaction, 7.81 g of a fraction was obtained. As a result of subjecting the obtained final reaction product to quantitative determination by GC, it was confirmed that 31.4 g (0.206 mol) of 2-pentyl-2-cyclopenten-1-one and 1.5 g (0.010 mol) of 2-pentylcyclopentan-1-one were produced. Further, it was confirmed that the yield of 2-pentyl-2-cyclopenten-1-one was 85%. The results including those for the other by-products are collectively shown in Table 1.

Comparative Example I-1

Dehydration Reaction Step

A 200 mL four-necked separable flask equipped with a dehydration apparatus was charged with 50.06 g (0.238 mol) of 2-(1-hydroxypentyl)-cyclopentan-1-one (purity: 81%) obtained according to the method described in Synthesis Example 1, and 0.13 g of the solid acid (shape: powder) obtained in Production Example 1. The contents of the flask were mixed with each other under heating in an atmosphere containing hydrogen and nitrogen at a volume ratio (hydrogen:nitrogen) of 1:7 at 150° C. under 101 kPa.

After 8 h from initiation of the reaction, 4.80 g of a fraction was obtained. As a result of subjecting the obtained final reaction product to quantitative determination by GC, it was confirmed that 30.0 g (0.197 mol) of 2-pentylidenecyclopentan-1-one were contained therein.

(Filtration Step)

The solid acid was removed from the resulting final reaction product by filtration to obtain 43.0 g of a filtrate. As a result, it was confirmed that the filtrate contained 29.3 g (0.193 mol) of 2-pentylidenecyclopentan-1-one.

(Isomerization Reaction Step)

A 200 mL four-necked separable flask equipped with a dehydration apparatus was charged with 43.0 g of the filtrate obtained in the above step and 4.17 g of 5% Pd/C (powder; 49% hydrous product; pH=5.8). The contents of the flask were mixed with each other under heating in an atmosphere containing hydrogen and nitrogen at a volume ratio (hydrogen:nitrogen) of 1:7 at 150° C. under 101 kPa.

After 9.5 h from initiation of the reaction, as a result of subjecting the obtained final reaction product to quantitative determination by GC, it was confirmed that 24.9 g (0.164 mol) of 2-pentyl-2-cyclopenten-1-one and 1.5 g (0.010 mol) of 2-pentylcyclopentan-1-one were produced. Further, it was confirmed that the yield of 2-pentyl-2-cyclopenten-1-one from 2-(1-hydroxypentyl)-cyclopentan-1-one through the three steps including the above dehydration reaction step, filtration step and isomerization reaction step was 71%. The results including those for the other by-products are collectively shown in Table 1.

TABLE 1

| | Examples | | | | | Comparative Example I-1 | |
|---|---|---|---|---|---|---|---|
| | I-1 | I-2 | I-3 | I-4 | I-5 | Dehydration reaction [3] | Isomerization reaction [3] |
| | Dehydration and isomerization reaction [3] | | | | | | |
| Acid | | | | | | | |
| Kind | $H_3PO_4$/C | $H_3PO_4$ | $H_3PO_4$ | $H_3PO_4$ | EtP—$AlPO_4$ | EtP—$AlPO_4$ | — |
| Amount [1] | 0.06% [8] | 0.04% | 0.38% | 0.14% [4] | 0.26% | 0.26% | — |
| Platinum group metal catalyst | | | | | | | |
| Kind | 5% Pd/C | 5% Pd/C | 5% Pd/C | 5% Pd/C | 5% Pd/C | — | 5% Pd/C |
| Amount [1], [2] | 3% | 5% | 5% | 5% [4] | 5% | — | 5% |
| Reaction time (h) | 10 | 12 | 11 | 9.5 | 15.5 | 8 | 9.5 |
| Composition of final reaction product (mol %) [1] | | | | | | | |
| Compound A [5] | 89 | 84 | 79 | 85 | 85 | | 71 |
| Compound B [6] | 7 | 5 | 4 | 8 | 4 | | 4 |
| Other low-boiling by-products | 1 | 2 | 2 | 0 | 2 | | 4 |
| Balance [7] | 3 | 9 | 15 | 7 | 9 | | 21 |
| Yield of compound A (%) [1] | 89 | 84 | 79 | 85 | 85 | | 71 |

Note
[1] Based on the amount of 2-(1-hydroxypentyl)-cyclopentan-1-one (raw material) charged.
[2] Including a weight of a carrier.
[3] Reaction conditions: temperature: 150° C; under an atmosphere containing a mixed gas $H_2$  $N_2$ ($H_2$:$N_2$ = 1:7); pressure: 101 kPa
[4] The catalyst used in Example I-3 was recycled. The amounts of the acid and catalyst were determined from analyzed values of phosphorus and palladium components, respectively.
[5] Compound A: 2-pentyl-2-cyclopenten-1-one.
[6] Compound 13: 2-pentylcyclopentan-1-one.
[7] Balance: high-boiling by-products.
[8] Content of P as calculated in terms of $Ha_3PO_4$.

Note
1) Based on the amount of 2-(1-hydroxypentyl)-cyclopentan-1-one (raw material) charged.
2) Including a weight of a carrier.
3) Reaction conditions: temperature: 150° C.; under an atmosphere containing a mixed gas $H_2$—$N_2$ ($H_2$:$N_2$=1:7); pressure: 101 kPa
4) The catalyst used in Example I-3 was recycled. The amounts of the acid and catalyst were determined from analyzed values of phosphorus and palladium components, respectively.
5) Compound A: 2-pentyl-2-cyclopenten-1-one.
6) Compound B: 2-pentylcyclopentan-1-one.
7) Balance: high-boiling by-products.
8) Content of P as calculated in terms of $Ha_3PO_4$.

Example I-6

In a nitrogen atmosphere, 208 g (1.56 mol) of dimethyl malonate (available from Aldrich Corp.) were dissolved in 63 g of anhydrous methanol (available from Aldrich Corp.), and the resulting solution was cooled to 0° C. and then mixed with 6.5 g (0.035 mol) of sodium methoxide (available from Wako Pure Chemical Industries, Ltd.; 30% methanol solution). Then, 183.48 g (1.01 mol) of 2-pentyl-2-cyclopenten-1-one (purity: 84%) were added dropwise to the resulting mixture at 0° C., followed by stirring the mixture. After completion of the reaction, the catalyst was neutralized and removed from the reaction mixture, and then the reaction mixture was subjected to distillation under reduced pressure to distill off methanol and unreacted dimethyl malonate therefrom to obtain 283.48 g of a Michael addition product (1,4-addition product).

The thus obtained Michael addition product (1,4-addition product) was charged into a reactor equipped with a distilling apparatus and heated to 215° C., followed by adding dropwise water thereto. While distilling off carbon dioxide and methanol generated, the contents of the reactor were subjected to the dropping reaction at 215° C. for 4 h. After completion of the reaction, 203.27 g of a crude reaction product was obtained.

The thus obtained crude reaction product was rectified to obtain methyl(3-oxo-2-pentylcyclopentyl)acetate (148.71 g). As a result, it was confirmed that the thus obtained methyl(3-oxo-2-pentylcyclopentyl)acetate had a fruity jasmine odor and was therefore an excellent perfume material.

Example I-7

An SUS 113 L reactor was charged with 66 kg (332 mol) of 2-(1-hydroxypentyl)-cyclopentan-1-one (purity: 85%) obtained according to the method described in Synthesis Example 1, 0.52 kg of a phosphoric acid-supporting activated carbon ($H_3PO_4$/C; powder, 8.7% hydrous product; phosphorus content: 0.010 (elemental analysis)), and 4.26 kg of 5% Pd/C (available from Evonik Degussa Co., Ltd.; powder, 53.6% hydrous product). The contents of the reactor were mixed with each other under heating in an atmosphere containing hydrogen and nitrogen at a volume ratio (hydrogen: nitrogen) of 1:8 at 140° C. under 101 kPa.

After 10 h from initiation of the reaction, 10.8 kg of a fraction was obtained. As a result of subjecting the obtained final reaction product to quantitative determination by GC, it was confirmed that 45.5 kg (299 mol) of 2-pentyl-2-cyclopenten-1-one were produced, and 2.0 kg (13 mol) of 2-pentylcyclopentan-1-one were by-produced. Further, it was confirmed that the yield of 2-pentyl-2-cyclopenten-1-one was 90%.

In a nitrogen atmosphere, 667 g (5.1 mol) of dimethyl malonate (available from Aldrich Corp.) were dissolved in 200 g of anhydrous methanol (available from Aldrich Corp.), and the resulting solution was cooled to 10° C. and then mixed with 21.5 g (0.18 mol) of sodium methoxide (available from Wako Pure Chemical Industries, Ltd.; 28% methanol solution). Then, 500 g (3.1 mol) of 2-pentyl-2-cyclopenten-1-one (purity: 95%) were added dropwise to the resulting mixture at 10° C., followed by stirring the mixture. After completion of the reaction, the catalyst was neutralized and removed from the reaction mixture, and then the reaction mixture was subjected to distillation under reduced pressure to distill off methanol and unreacted dimethyl malonate therefrom to obtain 871.6 g of a crude Michael addition product.

The thus obtained crude Michael addition product was charged into a reactor equipped with a distilling apparatus and heated to 185° C., followed by adding dropwise water thereto. While distilling off carbon dioxide and methanol generated, the contents of the reactor were subjected to the dropping reaction at 185° C. for 11 h. After completion of the reaction, 668.8 g of a crude reaction product was obtained.

The thus obtained crude reaction product (250.0 g) was rectified to obtain methyl(3-oxo-2-pentylcyclopentyl)acetate (192.1 g; yield based on 2-pentyl-2-cyclopenten-1-one: 73%). As a result, it was confirmed that the thus obtained methyl(3-oxo-2-pentylcyclopentyl)acetate had a fruity jasmine odor and was therefore an excellent perfume material.

Example II-1

(1) Step (A)

A 200 mL four-necked separable flask (made of glass) equipped with a dehydration apparatus was charged with 50 g (0.247 mol) of 2-(1-hydroxypentyl)-cyclopentan-1-one (purity: 84%) obtained according to the method described in Synthesis Example 1, 0.20 g of the solid acid (shape: powder) obtained in Production Example 1, and 5.1 g (dry weight: 2.6 g) of 5% Pd/C (available from N.E. ChemCat Corp.; Pd carbon powder, 49% hydrous product; pH=5.8). Then, under a stream of a mixed gas having a hydrogen concentration of 25% by volume and a nitrogen concentration of 75% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 3 h.

(2) Step (B)

Subsequently to the step (A), under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction was carried out at a temperature of from 140 to 147° C. (average temperature: 146° C.) for 12 h.

After completion of the step (B), as a result of subjecting the final reaction product to quantitative determination by GC, it was confirmed that 0.219 mol of 2-pentyl-2-cyclopenten-1-one was produced, and 0.012 mol of 2-pentylcyclopentan-1-one was by-produced. Further, it was confirmed that the yield of 2-pentyl-2-cyclopenten-1-one was 88.6%. The results including those for the other by-products are collectively shown in Table 2.

Example II-2

(1) Step (A)

A 200 mL four-necked separable flask (made of glass) equipped with a dehydration apparatus was charged with 50 g (0.244 mol) of 2-(1-hydroxypentyl)-cyclopentan-1-one (purity: 83%) obtained according to the method described in Synthesis Example 1, 0.20 g of the solid acid (shape: powder) obtained in Production Example 1, and 5.1 g (dry weight: 2.6 g) of 5% Pd/C (available from N.E. ChemCat Corp.). Then, under a stream of a mixed gas having a hydrogen concentration of 40% by volume and a nitrogen concentration of 60% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 3 h.

(2) Step (B)

Subsequently to the step (A), under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction was carried out at a temperature of from 140 to 147° C. (average temperature: 146° C.) for 10 h.

After completion of the step (B), as a result of subjecting the final reaction product to quantitative determination by GC, it was confirmed that 0.209 mol of 2-pentyl-2-cyclopenten-1-one was produced, and 0.018 mol of 2-pentylcyclopentan-1-one was by-produced. Further, it was confirmed that the yield of 2-pentyl-2-cyclopenten-1-one was 85.6%. The results including those for the other by-products are collectively shown in Table 2.

Comparative Example II-1

(1) Step (A)

A 200 mL four-necked separable flask (made of glass) equipped with a dehydration apparatus was charged with 50 g (0.242 mol) of 2-(1-hydroxypentyl)-cyclopentan-1-one (purity: 82%) obtained according to the method described in Synthesis Example 1, 0.20 g of the solid acid (shape: powder) obtained in Production Example 1, and 5.1 g (dry weight: 2.6 g) of 5% Pd/C (available from N.E. ChemCat Corp.). Then, under a stream of a gas having a hydrogen concentration of 100% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 2 h.

(2) Step (B)

Subsequently to the step (A), under a stream of a mixed gas having a hydrogen concentration of 50% by volume and a nitrogen concentration of 50% by volume at a flow rate of 0.2 N-mL/min per 1 g of pure 2-(1-hydroxypentyl)-cyclopentan-1-one as the raw material, the reaction was carried out at 140° C. for 3 h. Further, under a stream of a mixed gas having a hydrogen concentration of 20% by volume and a nitrogen concentration of 80% by volume, the reaction was carried out at 147° C. for 3 h.

After completion of the step (B), as a result of subjecting the final reaction product to quantitative determination by GC, it was confirmed that 0.200 mol of 2-pentyl-2-cyclopenten-1-one was produced, and 0.031 mol of 2-pentylcyclopentan-1-one was by-produced. Further, it was confirmed that the yield of 2-pentyl-2-cyclopenten-1-one was 82.8%. The results including those for the other by-products are collectively shown in Table 2.

Comparative Example II-2

(1) Step (A)

A 200 mL four-necked separable flask (made of glass) equipped with a dehydration apparatus was charged with 50 g (0.244 mol) of 2-(1-hydroxypentyl)-cyclopentan-1-one (purity: 83%) obtained according to the method described in Synthesis Example 1, 0.20 g of the solid acid (shape: powder) obtained in Production Example 1, and 5.1 g (dry weight: 2.6 g) of 5% Pd/C (available from N.E. ChemCat Corp.). Then, under a stream of a mixed gas having a hydrogen concentration of 50% by volume and a nitrogen concentration of 50% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 3 h.

(2) Step (B)

Subsequently to the step (A), under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction was carried out at a temperature of from 140° C. to 147° C. (average temperature: 145° C.) for 9 h.

After completion of the step (B), as a result of subjecting the final reaction product to quantitative determination by GC, it was confirmed that 0.205 mol of 2-pentyl-2-cyclopenten-1-one was produced, and 0.022 mol of 2-pentylcyclopentan-1-one was by-produced. Further, it was confirmed that the yield of 2-pentyl-2-cyclopenten-1-one was 84.3%. The results including those for the other by-products are collectively shown in Table 2.

Comparative Example II-3

A 200 mL four-necked separable flask equipped with a dehydration apparatus was charged with 50.8 g (0.243 mol) of 2-(1-hydroxypentyl)-cyclopentan-1-one (purity: 81%) obtained according to the method described in Synthesis Example 1, 0.13 g of the solid acid (shape: powder) obtained in Production Example 1, and 5.0 g (dry weight: 2.6 g) of 5% Pd/C (available from N.E. ChemCat Corp.). Then, under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction solution was heated to 150° C. under mixing.

After 15.5 h from initiation of the reaction at which the temperature reached 150° C., 7.81 g of a fraction was obtained. As a result of subjecting the obtained final reaction product to quantitative determination by GC, it was confirmed that 31.4 g (0.206 mol) of 2-pentyl-2-cyclopenten-1-one were produced, and 1.5 g (0.010 mol) of 2-pentylcyclopentan-1-one were by-produced. Further, it was confirmed that the yield of 2-pentyl-2-cyclopenten-1-one was 85.0%. The results including those for the other by-products are collectively shown in Table 2.

Example II-3

(1) Step (A)

A 2000 mL four-necked separable flask (made of glass) equipped with a dehydration apparatus was charged with 1395 g (6.95 mol) of 2-(1-hydroxypentyl)-cyclopentan-1-one (purity: 85%) obtained according to the method described in Synthesis Example 1, 3.6 g of the solid acid (shape: powder) obtained in Production Example 1, and 133.3 g (dry weight: 41.9 g) of 5% Pd/C (available from Evonik Degussa Japan Co., Ltd.; powder, 68.6% hydrous product). Then, under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 7 h.

(2) Step (B)

Subsequently to the step (A), under a stream of a mixed gas having a hydrogen concentration of 7.5% by volume and a nitrogen concentration of 92.5% by volume at a flow rate of 0.2 N-mL/min per 1 g of pure 2-(1-hydroxypentyl)-cyclopentan-1-one as the raw material, the reaction was carried out at 150° C. for 7 h.

After completion of the step (B), as a result of subjecting the final reaction product to quantitative determination by GC, it was confirmed that 6.13 mol of 2-pentyl-2-cyclopenten-1-one were produced, and 0.30 mol of 2-pentylcyclopentan-1-one was by-produced. Further, it was confirmed that the yield of 2-pentyl-2-cyclopenten-1-one was 88.1%. The results including those for the other by-products are collectively shown in Table 2.

Comparative Example II-4

(1) Step (A)

A 2000 mL four-necked separable flask (made of glass) equipped with a dehydration apparatus was charged with 1395 g (6.95 mol) of 2-(1-hydroxypentyl)-cyclopentan-1-one (purity: 85%) obtained according to the method described in Synthesis Example 1, 3.6 g of the solid acid (shape: powder) obtained in Production Example 1, and 133.3 g (dry weight: 41.9 g) of 5% Pd/C (available from Evonik Degussa Japan Co., Ltd.; powder, 49% hydrous product). Then, under a stream of a mixed gas having a hydrogen concentration of 12.5% by volume and a nitrogen concentration of 87.5% by volume at a flow rate of 0.2 N-mL/min per 1 g of pure 2-(1-hydroxypentyl)-cyclopentan-1-one as the raw material, the reaction solution was heated to 140° C. under mixing. After reaching the temperature of 140° C., the reaction was carried out for 7 h.

(2) Step (B)

Subsequently to the step (A), under a stream of a nitrogen gas solely at a flow rate of 0.2 N-mL/min per 1 g of pure 2-(1-hydroxypentyl)-cyclopentan-1-one as the raw material, the reaction was carried out at 150° C. for 15 h.

After completion of the step (B), as a result of subjecting the final reaction product to quantitative determination by GC, it was confirmed that 3.43 mol of 2-pentyl-2-cyclopenten-1-one were produced, and 0.14 mol of 2-pentylcyclopentan-1-one was by-produced. Further, it was confirmed that the yield of 2-pentyl-2-cyclopenten-1-one was 49.3%. The results including those for the other by-products are collectively shown in Table 2.

TABLE 2

|  | Examples | | Comparative Examples | | | Example | Comparative |
| --- | --- | --- | --- | --- | --- | --- | --- |
|  | II-1 | II-2 | II-1 | II-2 | II-3 | II-3 | Example II-4 |
| Acid Catalyst | | | | | | | |
| Kind | EtP—AlPO$_4$ | EtP—AlPO$_4$ | EtP—AlPO$_4$ | EtP—AlPO$_4$ | EtP—AlPO$_4$ | EtP—AlPO$_4$ | EtP—AlPO$_4$ |
| Catalyst amount [1] (mass %) | 0.4 | 0.4 | 0.4 | 0.4 | 0.3 | 0.3 | 0.3 |
| Platinum group metal catalyst | | | | | | | |
| Kind | Pd/C | Pd/C | Pd/C | Pd/C | Pd/C | Pd/C | Pd/C |
| Catalyst amount [1] (mass %) | 5 | 5 | 5 | 5 | 5 | 3 | 3 |
| Reaction temperature (° C.) | 140-147 | 140-147 | 140-147 | 140-147 | 150 | 140-150 | 140-150 |
| Reaction time (h) | 15 | 13 | 8 | 12 | 15.5 | 14 | 22 |
| Hydrogen gas concentration | | | | | | | |
| Step (A) (volume %) | 25 | 40 | 100 | 50 | 12.5 | 12.5 | 12.5 |
| Step (B) (volume %) | 12.5 | 12.5 | 50 → 20 | 12.5 | — | 7.5 | 0 |
| Reaction results | | | | | | | |
| Yield [2] (mol %) | 88.6 | 85.6 | 82.8 | 84.3 | 85.0 | 88.1 | 49.3 |
| Amount of saturated products [3] (mol %) | 5.0 | 7.4 | 12.9 | 8.9 | 3.8 | 4.3 | 2.1 |
| Amount of other by-products [4] (mol %) | 6.4 | 7.0 | 4.3 | 6.9 | 11.2 | 7.5 | 48.7 |

The notes for Table 2 are shown below.
[1] Catalyst amount = (mass of dried catalyst)/(mass of raw material) × 100
[2] Yield = (moles of 2-pentyl-2-cyclopenten-1-one in reaction product)/(moles of 2-(1-hydroxypentyl)-cyclopentan-1-one in raw material) × 100
[3] Amount of saturated products = (moles of 2-pen-tylcyclopentan-1-one in reaction product)/(moles of 2-(1-hydroxypentyl)-cyclopentan-1-one in raw material) × 100
[4] Amount of other by-products = (moles of by-products other than 2-pentylcyclopentan-1-one in reaction product)/(moles of 2-(1-hydroxypentyl)-cyclopentan-1-one in raw material) × 100

The notes for Table 2 are shown below.

1) Catalyst amount=(mass of dried catalyst)/(mass of raw material)×100

2) Yield=(moles of 2-pentyl-2-cyclopenten-1-one in reaction product)/(moles of 2-(1-hydroxypentyl)-cyclopentan-1-one in raw material)×100

3) Amount of saturated products=(moles of 2-pentylcyclopentan-1-one in reaction product)/(moles of 2-(1-hydroxypentyl)-cyclopentan-1-one in raw material)×100

4) Amount of other by-products=(moles of by-products other than 2-pentylcyclopentan-1-one in reaction product)/(moles of 2-(1-hydroxypentyl)-cyclopentan-1-one in raw material)×100

INDUSTRIAL APPLICABILITY

In accordance with the present invention, there are provided a process for producing 2-alkyl-2-cycloalken-1-ones with a high yield and a high purity, and a process for producing alkyl(3-oxo-2-alkylcycloalkyl)acetates which are useful as perfume materials, by using the 2-alkyl-2-cycloalken-1-ones.

The invention claimed is:

1. A process for producing a 2-alkyl-2-cycloalken-1-one represented by general formula (2), comprising dehydrating and isomerizing a 2-(1-hydroxyalkyl)cycloalkan-1-one represented by general formula (1) in the presence of an acid and a platinum group metal catalyst:

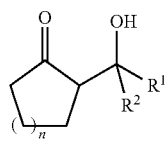

(1)

wherein n is an integer of 1 or 2; and $R^1$ and $R^2$ are each independently a hydrogen atom or an alkyl group having 1 to 8 carbon atoms with the proviso that $R^1$ and $R^2$ may form a cyclopentane ring or a cyclohexane ring through a carbon atom adjacent thereto; and

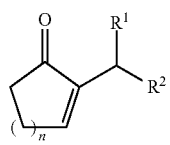

(2)

wherein n, $R^1$ and $R^2$ are the same as defined above.

2. The process for producing a 2-alkyl-2-cycloalken-1-one according to claim 1, wherein the acid has a first acid dissociation constant (pKa) of 0 or more as measured at 25° C.

3. The process for producing a 2-alkyl-2-cycloalken-1-one according to claim 1, wherein the acid is a solid acid.

4. The process for producing a 2-alkyl-2-cycloalken-1-one according to claim 3, wherein an amount (mmol/g) of acid sites of the solid acid from which $NH_3$ is desorbed at a temperature of from 100 to 250° C. is larger than an amount (mmol/g) of acid sites of the solid acid from which $NH_3$ is desorbed at a temperature higher than 250° C., as measured by an ammonia temperature-programmed desorption (TPD) method.

5. The process for producing a 2-alkyl-2-cycloalken-1-one according to claim 1, wherein said dehydrating and isomerizing comprises (A) and (B) where (B) is carried out after (A),
  (A): dehydrating and isomerizing the 2-(1-hydroxyalkyl)cycloalkan-1-one in an atmosphere in which a concentration of a hydrogen gas is from 5 to 45% by volume; and
  (B): dehydrating and isomerizing the 2-(1-hydroxyalkyl)cycloalkan-1-one in an atmosphere in which a concentration of a hydrogen gas is 1% by volume or higher, and is lower, by 2% by volume or more, than the concentration of the hydrogen gas in the atmosphere present in (A).

6. The process for producing a 2-alkyl-2-cycloalken-1-one according to claim 1, wherein the platinum group metal catalyst is a Pd-containing catalyst.

7. The process for producing a 2-alkyl-2-cycloalken-1-one according to claim 5, wherein the reactions of (A) and (B) are carried out at a temperature of from 0 to 300° C.

8. The process for producing a 2-alkyl-2-cycloalken-1-one according to claim 5, wherein a reaction time of (A) is from 5 to 50% of a total reaction time of (A) and (B).

9. A process for producing an alkyl(3-oxo-alkylcycloalkyl)acetate represented by general formula (4), comprising:
  reacting the 2-alkyl-2-cycloalken-1-one represented by general formula (2) which is obtained by the process as defined in claim 1, with a malonic acid diester represented by general formula (3); and
  reacting the resulting reaction product with water:

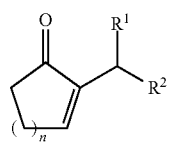 (2)

wherein n, $R^1$ and $R^2$ are the same as defined above;

 (3)

wherein $R^3$ is an alkyl group having 1 to 3 carbon atoms with the proviso that the two $R^3$ groups may be the same or different from each other; and

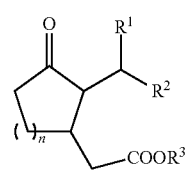 (4)

wherein n, $R^1$, $R^2$ and $R^3$ are the same as defined above.

* * * * *